United States Patent [19]
Tahara

[11] Patent Number: 6,112,752
[45] Date of Patent: Sep. 5, 2000

[54] LIQUID CONTAINER

[75] Inventor: Tomio Tahara, Tokyo, Japan

[73] Assignee: Kamaya Kagaku Kogyo Co., Ltd., Tokyo, Japan

[21] Appl. No.: 09/099,921

[22] Filed: Jun. 18, 1998

[30] Foreign Application Priority Data

Jun. 25, 1997 [JP] Japan ..................................... 9-184458

[51] Int. Cl.[7] ........................... A45D 33/00; A47L 23/04; B65D 47/10
[52] U.S. Cl. ........................... 132/293; 401/132; 222/107
[58] Field of Search ........................... 132/293; 401/132, 401/133, 183, 186, 271; 222/92, 96, 107, 491; 206/484

[56] References Cited

U.S. PATENT DOCUMENTS

| | | | |
|---|---|---|---|
| 4,301,923 | 11/1981 | Vuorento | 222/107 |
| 4,378,069 | 3/1983 | Franco | 222/107 |
| 5,348,191 | 9/1994 | Dekeyser | 222/107 |
| 5,380,110 | 1/1995 | Festa | 401/132 |
| 5,546,728 | 8/1996 | Dekeyser | 222/107 |

FOREIGN PATENT DOCUMENTS

| | | |
|---|---|---|
| 62-41701 | 10/1987 | Japan . |
| 8-198300 | 8/1996 | Japan . |

*Primary Examiner*—Todd E. Manahan
*Attorney, Agent, or Firm*—Baker Botts L.L.P.

[57] ABSTRACT

A liquid container has an automatic opening and closing mechanism preventing entry of air into the container, and is convenient for portable use. The liquid container comprises an upper shell and a lower bonded along their outer circumferential ends to define a flat liquid pool between them. At least one of the upper and lower shells is a thin skin member made of a flexible material to be deformable when depressed. The upper shell has formed a through hole communicating with the liquid pool, and a flexible film is bonded onto the upper shell to form the automatic opening and closing mechanism composed of a duct communicating with the through hole and an outlet communicating with the duct between the flexible film and the upper shell.

22 Claims, 7 Drawing Sheets

LIQUID CONTAINER

BACKGROUND OF THE INVENTION

This invention relates to a liquid container for containing a fluid or semi-fluid product, such as liquid cosmetic foundation, cosmetic lotion, medical paste, shoe paste, and wax, for example, and can be packaged in a flat case and carried for portable use.

Most conventional liquid containers for containing a fluid or semi-fluid products, such as liquid foundation, lotion or other cosmetic preparations, were bottles, jars, tubes, and so forth, combined with lids. These containers, however, were inconvenient for portable use and were not attractive in the mode of use.

As an improvement in these respects, there was proposed a liquid cosmetic cartridge disclosed in Japanese Utility Model Post-Examination Publication No. 62(1987)-41701. The cartridge comprises a resilient casing with a ship-shaped bottom and a lid member having a through hole and a liquid reservoir and mounted onto the resilient casing. When the resilient casing is compressed by depressing the lid member, the liquid is pushed out through the through hole.

When the liquid in the container decreases, the liquid remains in the center of the resilient casing, and can be discharged to the final amount thereof when the lid member is depressed to bring the inner surface of the lid member into contact with the bottom surface of the resilient casing. Thus, the container is convenient in the mode of supply of the content and for portable use by packaging in a compact, or other flat portable case.

The conventional cartridge, however, has no own means for air-tightly sealing the content, and involves the following problems.

One of the problems lies in that the cartridge itself cannot be used as an independent container because air-tight sealing of the content in the cartridge relies on a cover case.

Another problem lies in that it is difficult to air-tightly maintain a highly fluid content or a highly volatile content even by using the cover case. Moreover, air is inevitably introduced into the container upon restoration of the resilient casing after being depressed for supply of the content, and the content is likely to lose moisture and to change in quality due to the air.

Another problem lies in restoration of the resilient casing. Since the resilient restores its original aspect after being depressed, a user cannot readily know the amount of content remaining in the container. Moreover, since the resilient casing suctions air upon restoration, the content is jetted out scattered together with the air.

Therefore, the use of the cartridge has been limited only to particular kinds of liquid cosmetics.

SUMMARY OF THE INVENTION

It is therefore an object of the invention to provide a liquid container having an automatic opening and closing mechanism and usable either as a cartridge container or as a independent container.

Another object of the invention is to provide a liquid container having a flat shape and convenient for portable use.

Another object of the invention is to provide a liquid container which can be manufactured economically.

DESCRIPTION OF THE PREFERRED EMBODIMENTS

Explained below preferred embodiments of the invention in detail with reference to the drawings.

Figure 2A:
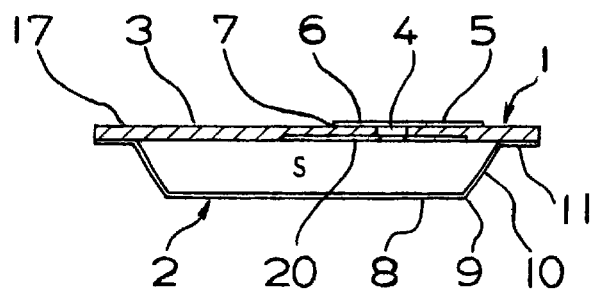
FIG. 2A is a cross-sectional view taken along the X—X line of FIG. 1.
Figure 2B:
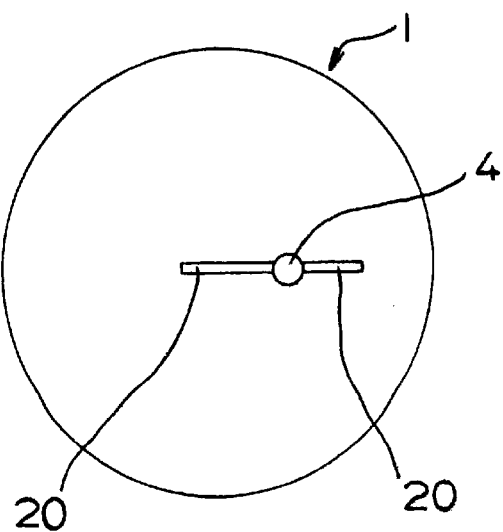
FIG. 2B is a bottom view of an upper shell of the container shown in FIG. 1.

As best shown in FIGS. 2A and 2B, a liquid container according to the invention generally comprises an upper shell 1 and a lower shell 2 which are combined and sealed together along their outer circumferential ends 17 to form a liquid pool S. At least one of the upper ane lower shells 1 and 2 is made of a flexible material in form of a thin skin which can be depressed.

FIGS. 1 through 9 show an embodiment of the invention in which the upper shell 1 is made of a hard material whereas the lower shell 2 is made of a flexible material.

Figure 1:
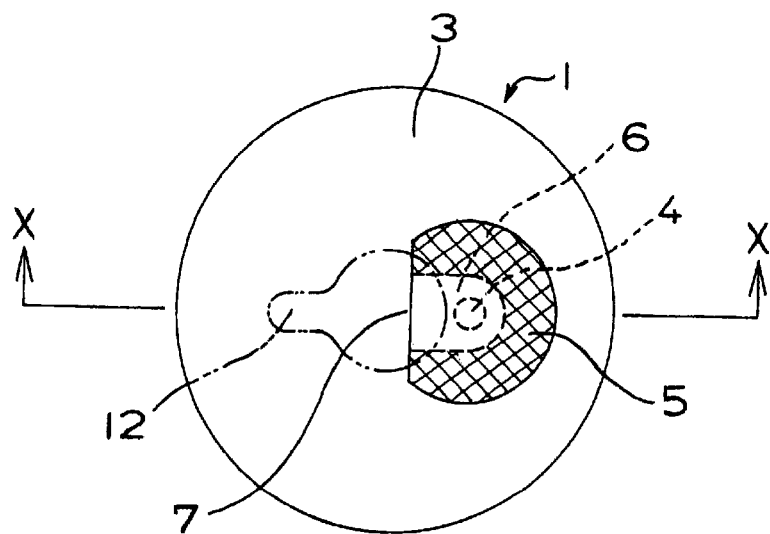
FIG. 1 is a plan view of a liquid container embodying the invention.

As best shown in FIGS. 1, 2A and 2B, the upper shell 1 is a disc-shaped member made of a hard synthetic resin material. The upper shell 1 has a through hole 4 passing through, and a flexible film 5 overlies the upper surface 3 of the upper shell 1 to cover the through hole 4. The film 5 is partly bonded onto the upper surface 3 in the region shown by cross-hatching in FIG. 1 by any known appropriate process, such as thermocompression bonding, thermowelding, heat bonding, hot-melt bonding using a hot-melt adhesive, for example.

The other part of the film 5 not bonded to the upper surface 3 is in close airtight contact with the upper surface 3 forms a duct 6 which communicates with the through hole 4 and opens to the exterior through an outlet 7 to form an automatic opening and closing mechanism. Additionally, the upper shell 1 has formed on its lower surface a groove 20 communicating with the through hole 4. The groove 20 functions as a capillary channel of the last amount of the content in the container when the bottom 8 of the lower shell 2 contacts the lower surface of the upper shell. Although the groove 20 is illustrated only here, it may be formed also in the subsequent embodiments.

The lower shell 2 is a thin-skin dish-shaped member made by a flexible sheet or film of a material such as elastomer, polyethylene, polypropylene, or the like. More specifically, the lower shell 2 is an integral member including a bottom plate 8, an annular side wall 10 rising diagonally from the extremity 9 of the bottom plate 8 and terminating at the upper end shaped in a horizontally extending annual flange 11.

After a content is filled in the lower shell 2, the upper shell 1 is put on the lower shell to cover it, and the outer circumferential portion 17 of the upper shell 2 is bonded to the flange 11 of the lower shell 2 to define the closed liquid pool S.

Numeral 12 denotes a tacky seal detachably applied onto the upper surface 3 of the upper shell 1 to close the outlet 7 and to prevent the content from being inadvertently pushed out before the start of use by a user.

Figure 3A:
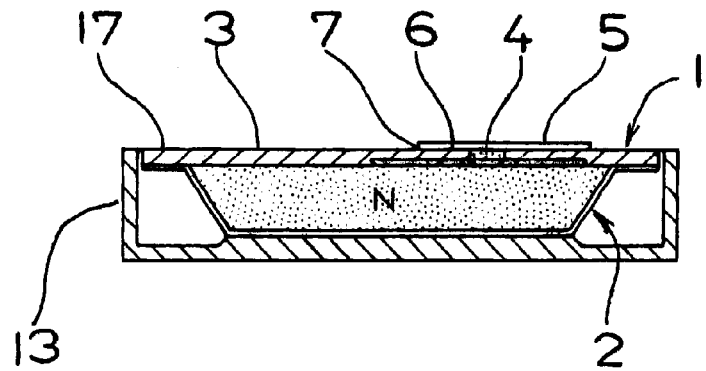
FIGS. 3A and 3B are cross-sectional views of the container shown in FIG. 1, which is packaged in a case.

The liquid container having the above-explained structure according to the embodiment has an entirely flat shape convenient for portable use. When the liquid container is carried, it is contained in a portable case 13 as shown in FIG. 3A (its lid is omitted from illustration).

Figure 3B:
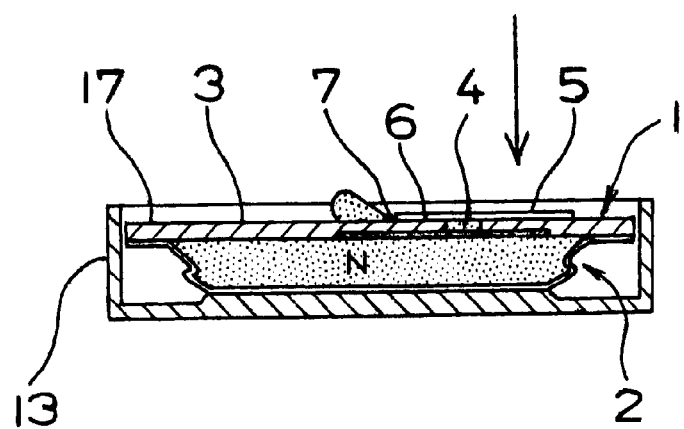

Upon using the content in the liquid container, a user may take out the liquid container from the portable case 13 compress it from upper and lower sides, or may depress the upper shell 1 of the liquid container held in the portable container 13 as shown in FIG. 3B. Responsively, the volume of the liquid pool S is deceased, and the content N overflows from the liquid pool S through the through hole 4 into the duct 6 between the non-bonded portion of the film 5 which flexibly deflects due to the overflow pressure of the content N and permits the content N to flow to and through the outlet 6 externally.

When the depression force is removed, the overflow pressure of the content N is lost, and the film 5 on the duct 6 simultaneously gets in close contact with the upper surface 3 of the upper shell 1 to automatically close the through hole 4.

The automatic opening and closing mechanism whose opening and shutting motion relies on the overflow pressure of the content N never introduces outer air into the liquid container. Therefore, as the content N decreases in the liquid pool S, the lower shell 2 flexibly deforms inwardly, and does not restore automatically. That is, the liquid container becomes thinner and thinner as its content N decreases, and a user can readily know the amount of the content N from the current outer appearance of the liquid container.

The automatic opening and closing mechanism used here has an additional effect. That is, since no air enters into liquid container, the content N therein is never exposed to air, and is never dried or changed in quality by air. Therefore, the liquid container is suitable for storage of semi-liquid cosmetic preparations, such as liquid foundation, which should maintain a certain amount of moisture, or volatile liquid cosmetic preparations. Moreover, since no air is introduced into the liquid container, the content N smoothly flows out from the outlet 7, without being jetted out together with air, when a user depresses the liquid container upon using it.

Figure 4:
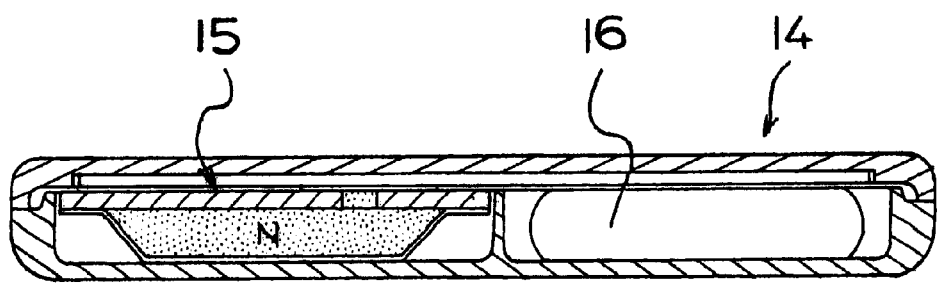
FIG. 4 is a cross-sectional view of the container shown in FIG. 1, which is packaged in a compact.

FIG. 4 is a cross-sectional view of the liquid container explained above, but prepared as a cartridge container 15 contained in a compact 14 together with a puff 16 so that a user can use the puff 16 on the cartridge container 15.

Figure 5A:
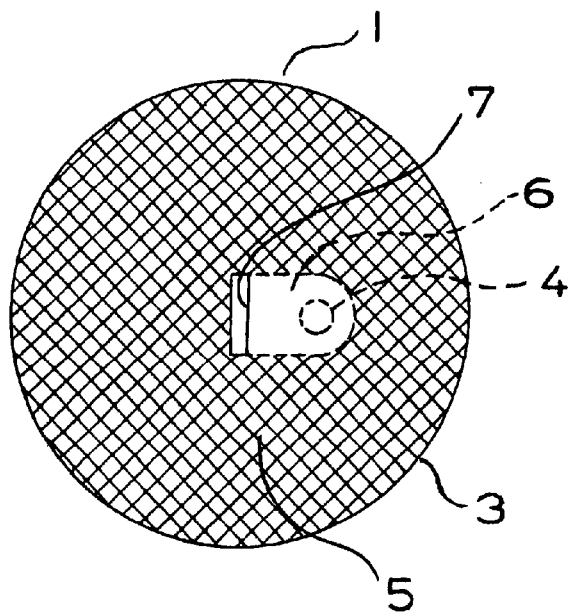
FIGS. 5A through 5C are plan views showing modifications of the automatic opening and closing mechanism of the liquid container.
Figure 5B:
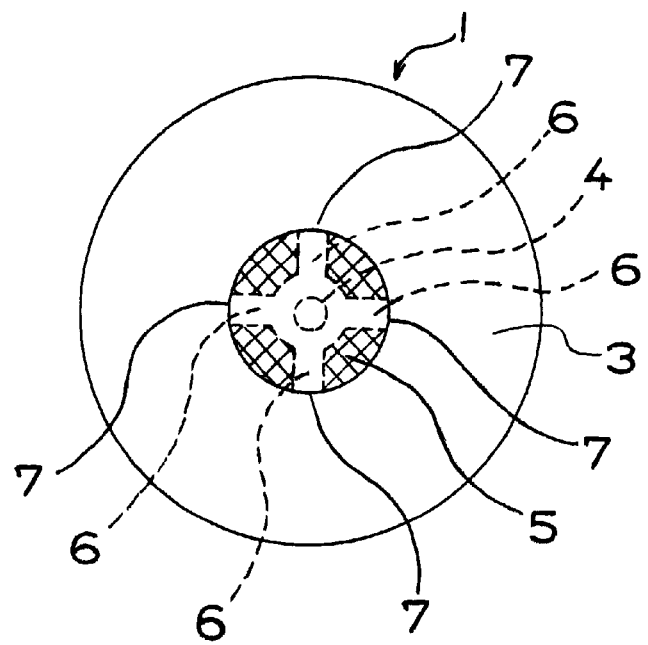
Figure 5C:
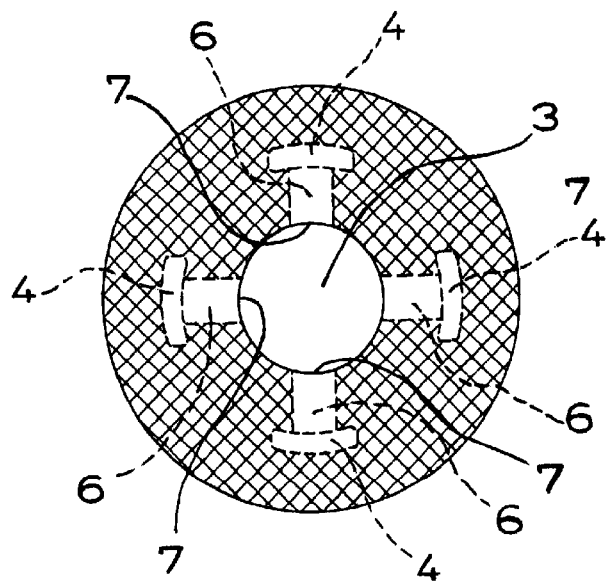

FIGS. 5A, 5B and 5C show modifications of the automatic opening and closing mechanism formed in the upper shell 1, which are especially suitable for storage of cosmetic preparations. In these and subsequent drawings, elements and parts common or equivalent to those of the foregoing embodiment are labeled with common numerals, and their explanation is omitted.

In the automatic opening and closing mechanism shown in FIG. 5A, the flexible film 5 covers the entirety of the upper surface 3 of the upper shell 1 to remove a difference in level by the thickness of the film 5 so that the puff 16 can smoothly run over the entire surface.

In the automatic opening and closing mechanism shown in FIG. 5B, a plurality of ducts 6 are formed to communicate a single through hole 4. Outlets 7 of the respective ducts 6 open to different directions to discharge the content over a wider area of the upper surface of the upper shell 1.

In the automatic opening and closing mechanism shown in FIG. 5C, a plurality of through holes 4 are provided, and ducts 6 extend from the respective through holes 4. Outlets 7 of the respective ducts 6 open toward the center to discharge the outlet onto the central area when the central portion of the upper shell 1 is depressed.

Figure 6:
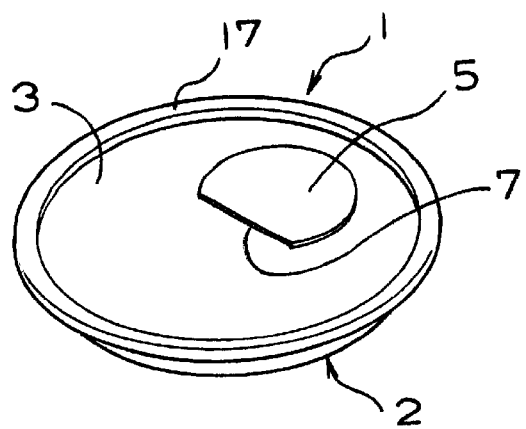
FIG. 6 is a perspective view showing a modified upper shell of the liquid container.

The liquid container according to the invention can be optimized for storage of a highly fluid content. A content with a high liquidity is more likely to flow out from the upper surface of the upper shell. To prevent it, the upper shell 1 preferably has a two-level member as shown in FIG. 6, in which the radially inner part there of is in a lower level than the outer circumferential end 17 to form a dish-like configuration.

Figure 7:
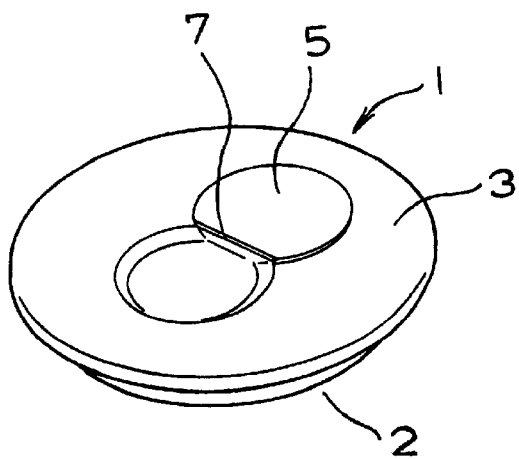
FIG. 7 is a perspective view showing a modified upper shell of the liquid container.

For storage of a highly fluid content which is used little by little, a cavity 18 for receiving a discharged amount of the content is preferably formed in the upper surface 3 of the upper shell 1 by depressing a part thereof in front of the outlet 7, as shown in FIG. 7.

Figure 8:
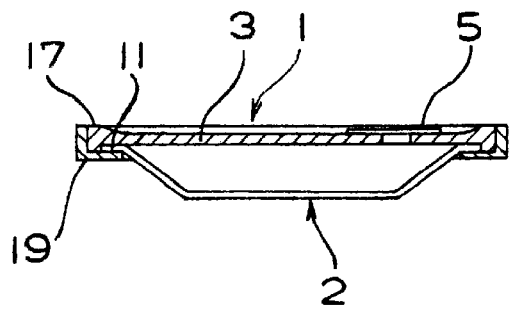
FIG. 8 is a cross-sectional view of a liquid container according to a further embodiment of the invention.

FIG. 8 shows another embodiment of the invention in which the upper shell 1 and the lower shell are joined together by means other than welding. That is, here is used an annular frame member 19 having an L-shaped cross-section including a vertically extending annular portion and a horizontally extending annular portion. After the flange portion 11 of the flexible lower shell 2 is set on the horizontally extending annular portion inside the frame member 19, the hard upper shell 1 is pressed into the frame member 19. Thus, the frame member 19 tightly holds the upper shell 1 and the lower shell 2 together. Where appropriate, the engage portions of these member 1, 2 and 19 may be welded to fix them more reliably by both the press-fitting mechanism and welding.

Figure 9A:
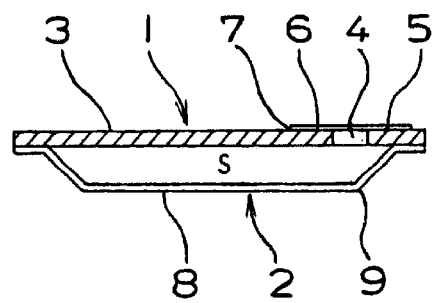
FIGS. 9A and 9B are cross-sectional views of a liquid container according to a further embodiment of the invention.
Figure 9B:
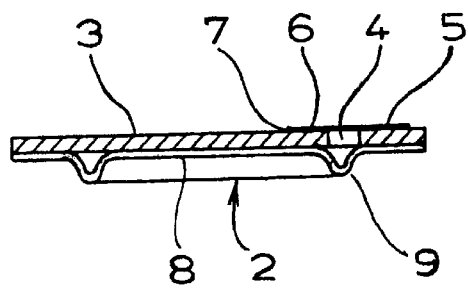

FIGS. 9A and 9B show another embodiment particularly suitable when the lower shell is made of an elastomer. The hard upper shell 1 used here has the through hole 4 in a location substantially aligned with the extremity 9 of the bottom plate 8 of the lower shell 2. As the content in the liquid container decreases, the dish-shaped lower shell 2 made of an elastomer gradually contracts to decrease its inner volume, projecting the extremity 9 of its bottom plate outwardly as shown in FIG. 9B. Even under the status, the content can be discharged to the last drop likely to remain on the extremity 9 because the through hole 4 is located above the extremity 9.

FIGS. 10 to 13 show some embodiments of the present invention using an upper shell 21 in form of a thin skin member flexibly deformable when depressed and a lower shell 22 made of a hard material. In these drawings, the automatic opening and closing mechanism and other elements or parts common to those of the foregoing embodiments are labeled with the same reference numerals, and their explanation is omitted.

Figure 10:
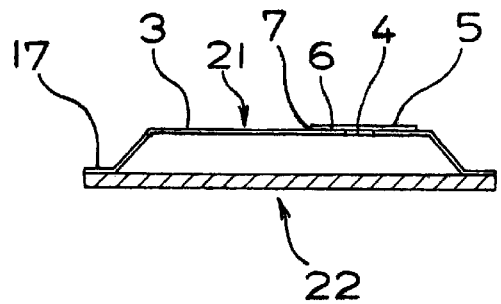
FIG. 10 is a cross-sectional view of a liquid container according to a further embodiment of the invention.

In the embodiment shown in FIG. 10, the upper shell 21 made of a flexible material and having formed the automatic opening and closing mechanism on its upper surface 3 is bonded with its outer circumferential portion 17 onto the lower shell 22 in form of a disk made of a hard material. The liquid container according to the embodiment is more convenient for a user to support it directly with his or her hand because the lower shell 22 is hard, and it is suitable for use outside the portable case.

Figure 11:
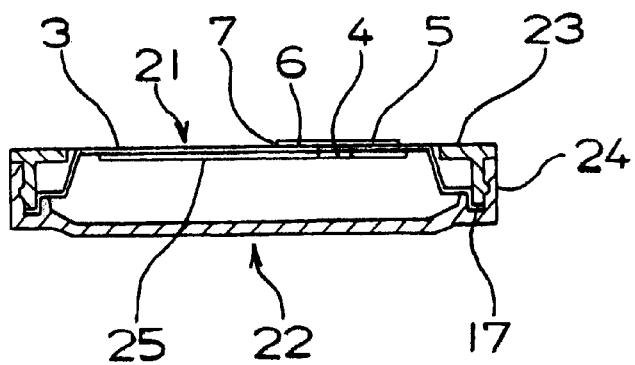
FIG. 11 is a cross-sectional view of a modified liquid container according to the invention.

The embodiment shown in FIG. 11 employs a construction facilitating assemblage of respective parts after filling the content. Here is used an annular frame member 23 having a shaped cross-section, and the hard lower shell 22 has formed a vertical wall 24. After the flexible upper shell 21 is bonded along its circumferential end 17 to the lower end of the frame member 23, the vertical portion of the frame member 23 is press-fit inside the vertical wall 24 of the lower shell 22. Thus, these elements 21, 22 and 23 are held in a tight engagement. Therefore, only by press-fitting the lower shell 22 onto the frame member 24 after filling the content in the upper shell 21 oriented upside down.

In any of the foregoing embodiments, a reinforcing plate 25 may be bonded to the lower surface of the upper shell 1 to ensure the upper shell 1 be depressed without distortion.

Figure 12A:
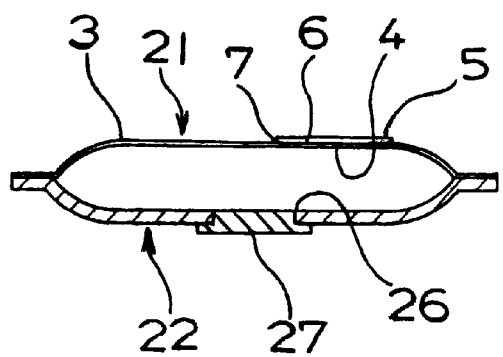
FIGS. 12A and 12B are cross-sectional views of a modified liquid container according to the invention.
Figure 12B:
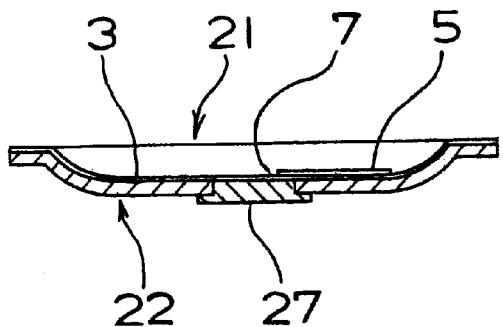

In the embodiment shown in FIG. 12A, both the flexible upper shell 21 and the hard lower shell 22 have dish-like configurations, similar in shape, which curve smoothly and continuously and have no angled corner. When the content decreases, the upper shell 21 depresses back into the lower shell 22 so that the content be more easily discharged to the final drop.

Additionally, an inlet hole 26 may be formed in the hard lower shell 22 so as to be used to fill the content into the liquid container. The inlet hole 26 is sealed with a plug member 27 after filling the content.

Figure 13:
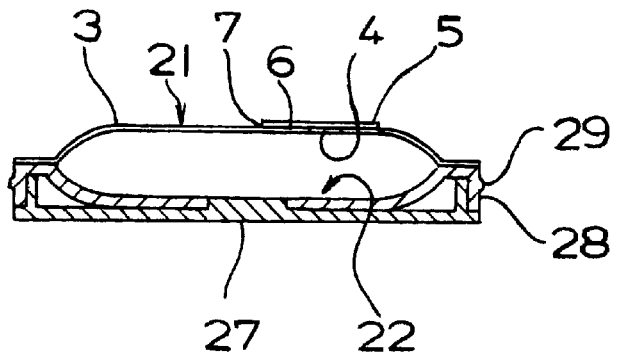
FIG. 13 is a cross-sectional view of a modified liquid container according to the invention.

In the embodiment shown in FIG. 13, the lower shell 22 has a skirt portion 29 along its outer circumferential end, and an engagement mechanism 29 is formed on the outer surface of the skirt portion 29 to removably engage in an appropriately structured portable case of compact. The liquid container according to the embodiment is suitable as a cartridge-type container.

Figure 14:
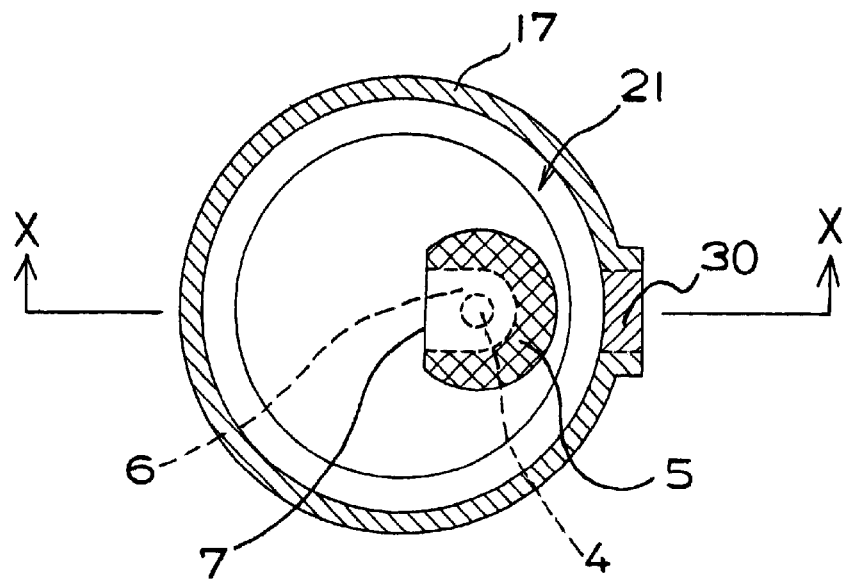
FIG. 14 is a plan view of a liquid container according to a further embodiment of the invention.
Figure 15:
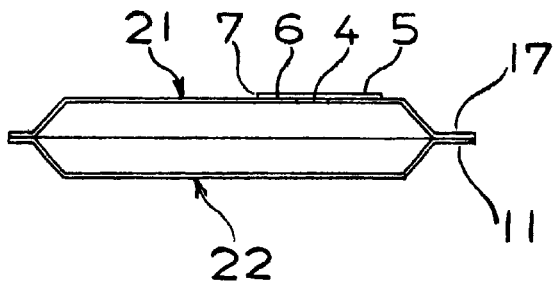
FIG. 15 is a cross-sectional view taken along the X—X line of FIG. 14.

FIGS. 14 and 5 show a further embodiment of the invention in which both the upper shell 21 and the lower shell 22 are made of a flexible material. These upper and lower shells 21, 22 are stacked and bonded to each other along their outer circumferential ends, excluding a small open portion 30, to form an empty container. The open portion 30 is sealed after a liquid is introduced into the container therethrough. The liquid container according to the embodiment is convenient for disposal because it is not bulky and can be folded small.

Although the foregoing embodiments have been explained and illustrated as using circular upper and lower shells, rectangular or any other configuration may be employed where appropriate. Additionally, the liquid container according to the invention can be used to store not only cosmetic preparations but also any other liquid products.

What is claimed is:

1. An apparatus comprising a liquid container having a generally flat configuration, said container including:
   an upper shell and a lower shell which are bonded along their outer circumferential ends to define a closed liquid pool therein, at least one of said upper shell and said lower shell being a thin skin member made of a flexible material and deformable when depressed; and
   at least one through hole formed through said upper shell; and
   a flexible film overlying at least an area on said upper shell which includes said through hole, and partly bonded onto said area on said upper shell to form an automatic opening and closing mechanism which includes a duct communicating at a first end with said through hole and at a second end with an outlet, said duct being defined between non-bonded portions of said film and said upper shell.

2. The apparatus of claim 1, wherein said through hole is offset from a center of said upper shell.

3. The apparatus of claim 1, wherein said upper shell has formed on a lower surface thereof a groove which communicates with said through hole.

4. The apparatus of claim 1, wherein said duct extends around said through hole.

5. The apparatus of claim 1, wherein said outlet is positioned at a central portion of said upper shell.

6. The apparatus of claim 1, wherein said upper shell is said thin skin member.

7. The apparatus of claim 1, further comprising a tacky seal detachably applied onto upper surfaces of said film and said upper shell to close said outlet and prevent the liquid from being inadvertently pushed out through said duct before a user removes said tacky seal.

8. The apparatus of claim 1, wherein said lower shell is said thin skin member; and wherein as said lower shell is depressed and deformed a first portion thereof moves to a position closely adjacent said upper shell while a second portion thereof remains spaced from said upper shell, said through hole being aligned with said second portion of said lower shell.

9. The apparatus of claim 1, including at least one annular frame member which is cooperable with said circumferential ends of said upper and lower shells to facilitate said bonding therebetween.

10. The apparatus of claim 1, wherein said lower shell has therethrough an inlet hole, and wherein said lower shell includes a plug member which is disposed in said inlet hole.

11. The apparatus of claim 1, wherein one of said upper and lower shells has in the region of said circumferential ends thereof an engagement portion operable to engage a case.

12. The apparatus of claim 1, wherein said circumferential ends are bonded along a first portion of the circumference thereof before said liquid pool is introduced into said container, and are bonded along a second portion of the circumference thereof after said liquid pool is introduced into said container, said liquid pool being introduced into said container between said circumferential ends of said upper and lower shells at said second portion thereof.

13. The apparatus of claim 1, wherein said upper shell has a depression in an exterior surface thereof, said flexible film being configured so that liquid exiting said outlet flows into said depression.

14. The apparatus of claim 1, including a case adapted to receive said container therein, and including a member disposed in said case and adapted for applying the liquid.

15. The apparatus of claim 1, wherein said duct includes a plurality of portions which extend outwardly in respective different radial directions with respect to said through hole.

16. An apparatus comprising a relatively flat liquid container which includes:

an upper shell and a lower shell which are bonded along their circumferential ends to define a closed liquid pool therein, said upper shell having formed on a lower surface thereof a groove, at least one of said upper shell and said lower shell being a thin skin member made of a flexible material and deformable when depressed;

at least one through hole formed through said upper shell and communicating at one end with said groove; and a flexible film overlying at least an area on said upper shell which includes said through hole, and partly bonded onto said area on said upper shell to form an automatic opening and closing mechanism which includes a duct extending around said through hole and communicating at a location remote from said through hole with an outlet, said duct being defined between non-bonded portions of said film and said upper shell.

17. The apparatus of claim 16, wherein said through hole is offset from a center of said upper shell.

18. The apparatus of claim 17, wherein said outlet is positioned at a central portion of said upper shell.

19. The apparatus of claim 18, wherein said upper shell is said thin skin member.

20. An apparatus comprising a liquid container having a generally flat configuration, said container including:

an upper shell and a lower shell which are bonded along their circumferential ends to define a closed liquid pool therein, at least one of said upper shell and said lower shell being a thin skin member made of a flexible material and deformable when depressed;

at least one through hole formed in said upper shell at a location spaced from said circumferential ends; and a flexible film overlying at least an area on said upper shell which includes said through hole, and partly bonded onto said area of said upper shell to form an automatic opening and closing mechanism which includes a duct communicating at a first end with said through hole and at a second end with an outlet, said duct being defined between non-bonded portions of said film and said upper shell.

21. An apparatus, comprising:

a shell portion having therein a chamber which contains a material that can flow and which is substantially free of air, said shell portion having a portion made of a flexible material which is deformable when manually pressed so as to decrease the size of said chamber therein, and having a through hole which extends through said shell portion from an interior thereof to an exterior thereof and which communicates with said chamber; and a flexible film portion overlying a region of said shell portion which includes said through hole, said film portion having a first portion which is bonded to said shell portion and having a second portion which is free of bonding to said shell portion, so that a duct is defined between said second portion and said shell portion, said duct communicating at one end with said through hole and at an opposite end with a region external to said shell portion, said second portion being movable between first and second positions in which said second portion is respectively spaced from and adjacent said shell portion, said film having a resilience which yieldably urges said second portion thereof toward said second position;

wherein when said second portion is in said second position, said second portion yieldably resists a flow of material out of said chamber through said duct and prevents a flow of air into said chamber through said duct, and wherein manual pressure applied to said portion of said shell causes material from said chamber to flex and move said second portion from said second position thereof to said first position thereof so that the material can flow out of said chamber through said duct, said resilience of said film portion returning said second portion thereof from said first position to said second position when the manual pressure decreases, said apparatus being free of structure which must be physically damaged before material from said chamber can flow through said duct.

22. The apparatus of claim 21, wherein said shell portion includes two parts which are bonded to each other at peripheral edges thereof, said chamber being located between said parts, and said through hole being spaced from said peripheral edges of each said parts.

* * * * *